(12) United States Patent
Gregorich et al.

(10) Patent No.: US 7,951,191 B2
(45) Date of Patent: May 31, 2011

(54) BIFURCATED STENT WITH ENTIRE CIRCUMFERENTIAL PETAL

(75) Inventors: Daniel Gregorich, St. Louis Park, MN (US); Michael P. Meyer, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 90 days.

(21) Appl. No.: 11/850,549

(22) Filed: Sep. 5, 2007

(65) Prior Publication Data
US 2008/0086197 A1 Apr. 10, 2008

Related U.S. Application Data

(60) Provisional application No. 60/850,458, filed on Oct. 10, 2006.

(51) Int. Cl.
*A61F 2/06* (2006.01)
(52) U.S. Cl. ...................... 623/1.35; 623/1.15
(58) Field of Classification Search ............ 623/1.35
See application file for complete search history.

(56) References Cited

U.S. PATENT DOCUMENTS

| | | |
|---|---|---|
| 4,309,994 A | 1/1982 | Grunwald |
| 4,769,005 A | 9/1988 | Ginsburg et al. |
| 4,774,949 A | 10/1988 | Fogarty |
| 4,896,670 A | 1/1990 | Crittenden |
| 4,905,667 A | 3/1990 | Foerster et al. |
| 4,906,244 A | 3/1990 | Pinchuk et al. |
| 4,935,190 A | 6/1990 | Tennerstedt |
| 4,994,071 A | 2/1991 | MacGregor |
| 5,037,392 A | 8/1991 | Hillstead |
| 5,053,007 A | 10/1991 | Euteneuer |
| 5,087,246 A | 2/1992 | Smith |
| 5,112,900 A | 5/1992 | Buddenhagen et al. |
| 5,147,302 A | 9/1992 | Euteneuer et al. |
| 5,163,989 A | 11/1992 | Campbell et al. |
| 5,209,799 A | 5/1993 | Vigil |
| 5,226,887 A | 7/1993 | Farr et al. |
| 5,306,246 A | 4/1994 | Sahatjian et al. |
| 5,318,587 A | 6/1994 | Davey |
| 5,342,307 A | 8/1994 | Euteneuer et al. |

(Continued)

FOREIGN PATENT DOCUMENTS

CA    2220864    7/1999

(Continued)

OTHER PUBLICATIONS

U.S. Appl. No. 60/844,011, filed Sep. 12, 2006; Inventor: Broome et al.

(Continued)

*Primary Examiner* — David Isabella
*Assistant Examiner* — Jacqueline Woznicki
(74) *Attorney, Agent, or Firm* — Vidas, Arrett & Steinkraus, P.A.

(57) ABSTRACT

A stent has a main body, which has a circumference that defines a primary lumen and longitudinal axis, which extends therethrough. A first region of the main body comprises at least one band disposed circumferentially about the longitudinal axis. A second region of the main body comprises a plurality of interconnected rings concentrically disposed about a side branch opening. An outermost ring extends fully about the circumference of the main body. Each of the rings consist of two longitudinally oriented elements and two circumferentially extending elements.

23 Claims, 4 Drawing Sheets

U.S. PATENT DOCUMENTS

| | | | |
|---|---|---|---|
| 5,342,387 A | 8/1994 | Summers | |
| 5,348,538 A | 9/1994 | Wang et al. | |
| 5,350,361 A | 9/1994 | Tsukashima et al. | |
| 5,358,475 A | 10/1994 | Mares et al. | |
| 5,387,235 A | 2/1995 | Chuter | |
| 5,403,340 A | 4/1995 | Wang et al. | |
| 5,447,497 A | 9/1995 | Sogard et al. | |
| 5,456,666 A | 10/1995 | Campbell et al. | |
| 5,456,712 A | 10/1995 | Maginot | |
| 5,458,572 A | 10/1995 | Campbell et al. | |
| 5,476,471 A | 12/1995 | Shifrin et al. | |
| 5,478,319 A | 12/1995 | Campbell et al. | |
| 5,487,730 A | 1/1996 | Marcadis et al. | |
| 5,523,092 A | 6/1996 | Hanson et al. | |
| 5,549,552 A | 8/1996 | Peters et al. | |
| 5,550,180 A | 8/1996 | Elsik et al. | |
| 5,556,383 A | 9/1996 | Wang et al. | |
| 5,591,228 A | 1/1997 | Edoga | |
| 5,607,444 A | 3/1997 | Lam | |
| 5,609,605 A | 3/1997 | Marshall et al. | |
| 5,609,627 A | 3/1997 | Goicoechea et al. | |
| 5,613,980 A | 3/1997 | Chauhan | |
| 5,617,878 A | 4/1997 | Taheri | |
| 5,632,762 A | 5/1997 | Myler | |
| 5,632,763 A | 5/1997 | Glastra | |
| 5,632,772 A | 5/1997 | Alcime et al. | |
| 5,636,641 A | 6/1997 | Fariabi | |
| 5,669,924 A | 9/1997 | Shaknovich | |
| 5,669,932 A | 9/1997 | Fischell et al. | |
| 5,676,697 A | 10/1997 | McDonald | |
| 5,683,450 A | 11/1997 | Goicoechea et al. | |
| 5,697,971 A | 12/1997 | Fischell et al. | |
| 5,707,348 A | 1/1998 | Krogh | |
| 5,709,713 A | 1/1998 | Evans et al. | |
| 5,718,684 A | 2/1998 | Gupta | |
| 5,718,724 A | 2/1998 | Goicoechea et al. | |
| 5,720,735 A | 2/1998 | Dorros | |
| 5,746,745 A | 5/1998 | Abele et al. | |
| 5,749,825 A | 5/1998 | Fischell et al. | |
| 5,749,890 A | 5/1998 | Shaknovich | |
| 5,755,734 A | 5/1998 | Richter et al. | |
| 5,755,735 A | 5/1998 | Richter et al. | |
| 5,755,771 A | 5/1998 | Penn et al. | |
| 5,755,773 A | 5/1998 | Evans et al. | |
| 5,755,778 A | 5/1998 | Kleshinski | |
| 5,782,906 A | 7/1998 | Marshall et al. | |
| 5,800,520 A | 9/1998 | Fogarty et al. | |
| 5,810,767 A | 9/1998 | Klein | |
| 5,824,036 A | 10/1998 | Lauterjung | |
| 5,824,040 A | 10/1998 | Cox et al. | |
| 5,827,320 A | 10/1998 | Richter et al. | |
| 5,830,182 A | 11/1998 | Wang et al. | |
| 5,833,657 A | 11/1998 | Reinhardt et al. | |
| 5,843,172 A | 12/1998 | Yan | |
| 5,851,464 A | 12/1998 | Davila et al. | |
| 5,868,777 A | 2/1999 | Lam | |
| 5,882,334 A | 3/1999 | Sepetka et al. | |
| 5,891,108 A | 4/1999 | Leone et al. | |
| 5,893,887 A | 4/1999 | Jayaraman | |
| 5,906,640 A | 5/1999 | Penn et al. | |
| 5,922,020 A | 7/1999 | Klein et al. | |
| 5,922,021 A | 7/1999 | Jang | |
| 5,951,941 A | 9/1999 | Wang et al. | |
| 5,961,548 A | 10/1999 | Shmulewitz | |
| 5,972,017 A | 10/1999 | Berg et al. | |
| 5,972,027 A | 10/1999 | Johnson | |
| 6,013,054 A | 1/2000 | Jiun Yan | |
| 6,013,055 A | 1/2000 | Bampos et al. | |
| 6,013,091 A | 1/2000 | Ley et al. | |
| 6,017,324 A | 1/2000 | Tu et al. | |
| 6,017,363 A | 1/2000 | Hojeibane | |
| 6,030,414 A | 2/2000 | Taheri | |
| 6,033,380 A | 3/2000 | Butaric et al. | |
| 6,033,433 A | 3/2000 | Ehr et al. | |
| 6,033,434 A | 3/2000 | Borghi | |
| 6,033,435 A | 3/2000 | Penn et al. | |
| 6,048,361 A | 4/2000 | Von Oepen | |
| 6,056,775 A | 5/2000 | Borghi et al. | |
| 6,059,824 A | 5/2000 | Taheri | |
| 6,068,655 A | 5/2000 | Seguin et al. | |
| 6,071,285 A | 6/2000 | Lashinski et al. | |
| 6,071,305 A | 6/2000 | Brown et al. | |
| 6,086,611 A | 7/2000 | Duffy et al. | |
| 6,093,203 A | 7/2000 | Uflacker | |
| 6,096,070 A | 8/2000 | Ragheb et al. | |
| 6,096,073 A | 8/2000 | Webster et al. | |
| 6,099,497 A | 8/2000 | Adams et al. | |
| 6,113,579 A | 9/2000 | Eidenschink et al. | |
| 6,117,117 A | 9/2000 | Mauch | |
| 6,117,156 A | 9/2000 | Richter et al. | |
| 6,123,721 A | 9/2000 | Jang | |
| 6,126,652 A | 10/2000 | McLeod et al. | |
| 6,129,738 A | 10/2000 | Lashinski et al. | |
| 6,129,754 A | 10/2000 | Kanesaka et al. | |
| 6,135,982 A | 10/2000 | Campbell | |
| 6,142,973 A | 11/2000 | Carleton et al. | |
| 6,143,002 A | 11/2000 | Vietmeier | |
| 6,146,356 A | 11/2000 | Wang et al. | |
| 6,159,238 A | 12/2000 | Killion et al. | |
| 6,165,195 A | 12/2000 | Wilson et al. | |
| 6,168,621 B1 | 1/2001 | Vrba | |
| 6,171,278 B1 | 1/2001 | Wang et al. | |
| 6,183,509 B1 | 2/2001 | Dibie | |
| 6,190,404 B1 | 2/2001 | Palmaz et al. | |
| 6,203,568 B1 | 3/2001 | Lombardi et al. | |
| 6,206,915 B1 | 3/2001 | Fagan et al. | |
| 6,206,916 B1 | 3/2001 | Furst | |
| 6,210,380 B1 | 4/2001 | Mauch | |
| 6,210,429 B1 | 4/2001 | Vardi et al. | |
| 6,210,433 B1 | 4/2001 | Larre | |
| 6,210,436 B1 | 4/2001 | Weadock | |
| 6,231,598 B1 | 5/2001 | Berry et al. | |
| 6,240,616 B1 | 6/2001 | Yan | |
| 6,241,762 B1 | 6/2001 | Shanley | |
| 6,253,443 B1 | 7/2001 | Johnson | |
| 6,254,593 B1 | 7/2001 | Wilson | |
| 6,254,632 B1 | 7/2001 | Wu et al. | |
| 6,258,115 B1 | 7/2001 | Dubrul | |
| 6,258,116 B1 | 7/2001 | Hojeibane | |
| 6,258,121 B1 | 7/2001 | Yang et al. | |
| 6,261,305 B1 | 7/2001 | Marotta et al. | |
| 6,261,316 B1 | 7/2001 | Shaolian et al. | |
| 6,261,320 B1 | 7/2001 | Tam et al. | |
| 6,264,662 B1 | 7/2001 | Lauterjung | |
| 6,264,686 B1 | 7/2001 | Rieu et al. | |
| 6,273,908 B1 | 8/2001 | Ndondo-Lay | |
| 6,273,913 B1 | 8/2001 | Wright et al. | |
| 6,280,413 B1 | 8/2001 | Clark et al. | |
| 6,287,628 B1 | 9/2001 | Hossainy et al. | |
| 6,290,673 B1 | 9/2001 | Shanley | |
| 6,293,967 B1 | 9/2001 | Shanley | |
| 6,293,968 B1 | 9/2001 | Taheri | |
| 6,325,826 B1 | 12/2001 | Vardi et al. | |
| 6,328,925 B1 | 12/2001 | Wang et al. | |
| 6,334,864 B1 | 1/2002 | Amplatz et al. | |
| 6,334,870 B1 | 1/2002 | Ehr et al. | |
| 6,346,089 B1 | 2/2002 | Dibie | |
| 6,348,065 B1 | 2/2002 | Brown et al. | |
| 6,355,060 B1 | 3/2002 | Lenker et al. | |
| 6,358,552 B1 | 3/2002 | Mandralis et al. | |
| 6,361,544 B1 | 3/2002 | Wilson et al. | |
| 6,361,555 B1 | 3/2002 | Wilson | |
| 6,379,381 B1 | 4/2002 | Hossainy et al. | |
| 6,383,213 B2 | 5/2002 | Wilson et al. | |
| 6,395,018 B1 | 5/2002 | Castaneda | |
| 6,395,326 B1 | 5/2002 | Castro et al. | |
| 6,406,457 B1 | 6/2002 | Wang et al. | |
| 6,423,091 B1 | 7/2002 | Hojeibane | |
| 6,436,104 B2 | 8/2002 | Hojeibane | |
| 6,436,134 B2 | 8/2002 | Richter et al. | |
| 6,478,816 B1 | 11/2002 | Kveen et al. | |
| 6,491,666 B1 | 12/2002 | Santini, Jr. et al. | |
| 6,506,437 B1 | 1/2003 | Harish et al. | |
| 6,508,836 B2 | 1/2003 | Wilson et al. | |
| 6,517,558 B2 | 2/2003 | Gittings et al. | |
| 6,520,987 B1 * | 2/2003 | Plante | 623/1.16 |
| 6,520,988 B1 | 2/2003 | Colombo et al. | |

| | | |
|---|---|---|
| 6,527,762 B1 | 3/2003 | Santini, Jr. et al. |
| 6,527,799 B2 | 3/2003 | Shanley |
| 6,537,256 B2 | 3/2003 | Santini, Jr. et al. |
| 6,540,779 B2 | 4/2003 | Richter et al. |
| 6,551,351 B2 | 4/2003 | Smith et al. |
| 6,551,838 B2 | 4/2003 | Santini, Jr. et al. |
| 6,558,422 B1 | 5/2003 | Baker et al. |
| 6,562,065 B1 | 5/2003 | Shanley |
| 6,579,309 B1 | 6/2003 | Loos et al. |
| 6,579,312 B2 | 6/2003 | Wilson et al. |
| 6,582,394 B1 | 6/2003 | Reiss et al. |
| 6,596,020 B2 | 7/2003 | Vardi et al. |
| 6,599,316 B2 | 7/2003 | Vardi et al. |
| 6,638,302 B1 | 10/2003 | Curcio et al. |
| 6,645,242 B1 | 11/2003 | Quinn |
| 6,656,162 B2 | 12/2003 | Santini, Jr. et al. |
| 6,669,683 B2 | 12/2003 | Santini, Jr. et al. |
| 6,689,156 B1 | 2/2004 | Davidson et al. |
| 6,692,483 B2 | 2/2004 | Vardi et al. |
| 6,695,877 B2 | 2/2004 | Brucker et al. |
| 6,706,062 B2 | 3/2004 | Vardi et al. |
| 6,709,379 B1 | 3/2004 | Brandau et al. |
| 6,713,119 B2 | 3/2004 | Hossainy et al. |
| 6,730,064 B2 | 5/2004 | Ragheb et al. |
| 6,749,628 B1 | 6/2004 | Callol et al. |
| 6,758,859 B1 | 7/2004 | Dang et al. |
| 6,764,507 B2 | 7/2004 | Shanley et al. |
| 6,773,429 B2 | 8/2004 | Sheppard, Jr. et al. |
| 6,776,793 B2 | 8/2004 | Brown et al. |
| 6,783,543 B2 | 8/2004 | Jang |
| 6,790,228 B2 | 9/2004 | Hossainy et al. |
| 6,811,566 B1 | 11/2004 | Penn et al. |
| 6,827,250 B2 | 12/2004 | Uhland et al. |
| 6,835,203 B1 | 12/2004 | Vardi et al. |
| 6,858,038 B2 | 2/2005 | Heuser |
| 6,884,258 B2 | 4/2005 | Vardi et al. |
| 6,896,699 B2 | 5/2005 | Wilson et al. |
| 6,904,658 B2 | 6/2005 | Hines |
| 6,932,837 B2 | 8/2005 | Amplatz et al. |
| 6,946,092 B1 | 9/2005 | Bertolino et al. |
| 6,955,687 B2 | 10/2005 | Richter et al. |
| 6,955,688 B2 | 10/2005 | Wilson et al. |
| 6,962,602 B2 | 11/2005 | Vardi et al. |
| 6,989,071 B2 | 1/2006 | Kocur et al. |
| 7,018,400 B2 | 3/2006 | Lashinski et al. |
| 7,041,130 B2 | 5/2006 | Santini, Jr. et al. |
| 7,052,488 B2 | 5/2006 | Uhland |
| 7,056,323 B2 | 6/2006 | Mareiro et al. |
| 7,056,338 B2 | 6/2006 | Shanley et al. |
| 7,060,091 B2 | 6/2006 | Killion et al. |
| 7,070,616 B2 | 7/2006 | Majercak et al. |
| 7,160,321 B2 | 1/2007 | Shanley et al. |
| 7,169,175 B2 | 1/2007 | Cottone, Jr. et al. |
| 7,169,179 B2 | 1/2007 | Shanley et al. |
| 7,179,288 B2 | 2/2007 | Shanley |
| 7,179,289 B2 | 2/2007 | Shanley |
| 7,208,010 B2 | 4/2007 | Shanley et al. |
| 7,208,011 B2 | 4/2007 | Shanley et al. |
| 7,220,275 B2 | 5/2007 | Davidson et al. |
| 2001/0003161 A1 | 6/2001 | Vardi et al. |
| 2001/0004706 A1 | 6/2001 | Hojeibane |
| 2001/0004707 A1 | 6/2001 | Dereume et al. |
| 2001/0012927 A1 | 8/2001 | Mauch |
| 2001/0016766 A1 | 8/2001 | Vardi et al. |
| 2001/0016767 A1 | 8/2001 | Wilson et al. |
| 2001/0016768 A1 | 8/2001 | Wilson et al. |
| 2001/0025195 A1 | 9/2001 | Shaolian et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0039448 A1 | 11/2001 | Dibie |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0035392 A1 | 3/2002 | Wilson |
| 2002/0038146 A1 | 3/2002 | Harry |
| 2002/0042650 A1 | 4/2002 | Vardi et al. |
| 2002/0052648 A1 | 5/2002 | McGuckin, Jr. et al. |
| 2002/0072790 A1 | 6/2002 | McGuckin, Jr. et al. |
| 2002/0095208 A1 | 7/2002 | Gregorich et al. |
| 2002/0111675 A1 | 8/2002 | Wilson |
| 2002/0156516 A1 | 10/2002 | Vardi et al. |
| 2002/0156517 A1 | 10/2002 | Perouse |
| 2002/0163104 A1 | 11/2002 | Motsenbocker et al. |
| 2002/0165603 A1* | 11/2002 | Thornton et al. ............ 623/1.13 |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0183763 A1 | 12/2002 | Callol et al. |
| 2002/0193872 A1 | 12/2002 | Trout, III et al. |
| 2002/0193873 A1 | 12/2002 | Brucker et al. |
| 2003/0009209 A1 | 1/2003 | Hojeibane |
| 2003/0028233 A1 | 2/2003 | Vardi et al. |
| 2003/0050688 A1 | 3/2003 | Fischell et al. |
| 2003/0055378 A1 | 3/2003 | Wang et al. |
| 2003/0055483 A1 | 3/2003 | Gumm |
| 2003/0074047 A1 | 4/2003 | Richter |
| 2003/0083687 A1 | 5/2003 | Pallazza |
| 2003/0093109 A1 | 5/2003 | Mauch |
| 2003/0097169 A1 | 5/2003 | Brucker |
| 2003/0105511 A1 | 6/2003 | Welsh et al. |
| 2003/0114912 A1 | 6/2003 | Sequin et al. |
| 2003/0125791 A1 | 7/2003 | Sequin et al. |
| 2003/0125802 A1 | 7/2003 | Callol et al. |
| 2003/0135259 A1 | 7/2003 | Simso |
| 2003/0163157 A1 | 8/2003 | McMorrow et al. |
| 2003/0167085 A1 | 9/2003 | Shanley |
| 2003/0181923 A1 | 9/2003 | Vardi |
| 2003/0195606 A1 | 10/2003 | Davidson et al. |
| 2003/0199970 A1 | 10/2003 | Shanley |
| 2004/0006381 A1 | 1/2004 | Sequin et al. |
| 2004/0015227 A1 | 1/2004 | Vardi et al. |
| 2004/0044396 A1 | 3/2004 | Clerc et al. |
| 2004/0059406 A1 | 3/2004 | Cully et al. |
| 2004/0068161 A1 | 4/2004 | Couvillon, Jr. |
| 2004/0073294 A1 | 4/2004 | Diaz et al. |
| 2004/0088007 A1 | 5/2004 | Eidenschink |
| 2004/0093071 A1 | 5/2004 | Jang |
| 2004/0117003 A1 | 6/2004 | Ouriel et al. |
| 2004/0122505 A1 | 6/2004 | Shanley |
| 2004/0122506 A1 | 6/2004 | Shanley et al. |
| 2004/0127976 A1 | 7/2004 | Diaz |
| 2004/0127977 A1 | 7/2004 | Shanley |
| 2004/0133268 A1 | 7/2004 | Davidson et al. |
| 2004/0138732 A1 | 7/2004 | Suhr et al. |
| 2004/0138737 A1* | 7/2004 | Davidson et al. ............ 623/1.35 |
| 2004/0142014 A1 | 7/2004 | Livack et al. |
| 2004/0143321 A1 | 7/2004 | Livack et al. |
| 2004/0143322 A1 | 7/2004 | Livack et al. |
| 2004/0148006 A1 | 7/2004 | Davidson et al. |
| 2004/0148012 A9 | 7/2004 | Jang |
| 2004/0172121 A1 | 9/2004 | Eidenschink et al. |
| 2004/0186560 A1 | 9/2004 | Alt |
| 2004/0202692 A1 | 10/2004 | Shanley et al. |
| 2004/0204750 A1 | 10/2004 | Dinh |
| 2004/0215227 A1 | 10/2004 | McMorrow et al. |
| 2004/0220661 A1 | 11/2004 | Shanley et al. |
| 2004/0225345 A1 | 11/2004 | Fischell et al. |
| 2004/0236408 A1 | 11/2004 | Shanley |
| 2004/0249449 A1 | 12/2004 | Shanley et al. |
| 2004/0267352 A1 | 12/2004 | Davidson et al. |
| 2005/0004656 A1 | 1/2005 | Das |
| 2005/0010278 A1* | 1/2005 | Vardi et al. .................... 623/1.15 |
| 2005/0015108 A1 | 1/2005 | Williams et al. |
| 2005/0015135 A1 | 1/2005 | Shanley |
| 2005/0043816 A1 | 2/2005 | Datta et al. |
| 2005/0060027 A1 | 3/2005 | Khenansho et al. |
| 2005/0096726 A1 | 5/2005 | Sequin et al. |
| 2005/0102017 A1 | 5/2005 | Mattison |
| 2005/0102021 A1 | 5/2005 | Osborne |
| 2005/0102023 A1* | 5/2005 | Yadin et al. .................... 623/1.15 |
| 2005/0119731 A1 | 6/2005 | Brucker et al. |
| 2005/0125076 A1 | 6/2005 | Ginn |

| | | |
|---|---|---|
| 2005/0131526 A1 | 6/2005 | Wong |
| 2005/0149161 A1 | 7/2005 | Eidenschink et al. |
| 2005/0154442 A1 | 7/2005 | Eidenschink et al. |
| 2005/0154444 A1 | 7/2005 | Quadri |
| 2005/0183259 A1 | 8/2005 | Eidenschink et al. |
| 2005/0187602 A1 | 8/2005 | Eidenschink |
| 2005/0187611 A1 | 8/2005 | Ding et al. |
| 2005/0192657 A1 | 9/2005 | Colen et al. |
| 2005/0209673 A1 | 9/2005 | Shaked |
| 2005/0222668 A1 | 10/2005 | Schaeffer et al. |
| 2005/0228483 A1 | 10/2005 | Kaplan et al. |
| 2005/0273149 A1 | 12/2005 | Tran et al. |
| 2006/0015134 A1 | 1/2006 | Trinidad |
| 2006/0034884 A1 | 2/2006 | Stenzel |
| 2006/0036315 A1* | 2/2006 | Yadin et al. .................. 623/1.35 |
| 2006/0041303 A1 | 2/2006 | Israel |
| 2006/0045901 A1 | 3/2006 | Weber |
| 2006/0079956 A1 | 4/2006 | Eigler et al. |
| 2006/0088654 A1 | 4/2006 | Ding et al. |
| 2006/0093643 A1 | 5/2006 | Stenzel |
| 2006/0100686 A1 | 5/2006 | Bolduc |
| 2006/0122698 A1 | 6/2006 | Spencer et al. |
| 2006/0173528 A1 | 8/2006 | Feld et al. |
| 2006/0206188 A1 | 9/2006 | Weber et al. |
| 2006/0287712 A1 | 12/2006 | Eidenschink |
| 2007/0005126 A1 | 1/2007 | Tischler |
| 2007/0050016 A1 | 3/2007 | Gregorich et al. |
| 2007/0073376 A1 | 3/2007 | Krolik et al. |
| 2007/0073384 A1 | 3/2007 | Brown et al. |
| 2007/0100434 A1 | 5/2007 | Gregorich et al. |
| 2007/0142902 A1* | 6/2007 | Yadin ........................... 623/1.16 |
| 2007/0150046 A1* | 6/2007 | Meyer et al. ................. 623/1.15 |
| 2007/0173787 A1 | 7/2007 | Huang et al. |
| 2007/0173923 A1 | 7/2007 | Savage et al. |
| 2007/0208414 A1* | 9/2007 | Sorenson et al. ............ 623/1.16 |
| 2007/0260303 A1* | 11/2007 | Hegg ............................ 623/1.16 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| DE | 19921788 | 11/2000 |
| EP | 0479730 | 10/1991 |
| EP | 0565796 | 10/1993 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0950386 | 10/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 94/23787 | 10/1994 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/23228 | 6/1998 |
| WO | 98/36709 | 8/1998 |
| WO | 98/36784 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15108 | 4/1999 |
| WO | 99/15109 | 4/1999 |
| WO | 99/23977 | 5/1999 |
| WO | 99/24104 | 5/1999 |
| WO | 99/29262 | 6/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/17577 | 3/2001 |
| WO | 01/21095 | 3/2001 |
| WO | 01/21109 | 3/2001 |
| WO | 01/21244 | 3/2001 |
| WO | 01/26584 | 4/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45594 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/66036 | 9/2001 |
| WO | 01/70294 | 9/2001 |
| WO | 01/70299 | 9/2001 |
| WO | 01/74273 | 10/2001 |
| WO | 01/89409 | 11/2001 |
| WO | 01/91918 | 12/2001 |
| WO | 01/93781 | 12/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |

| | | |
|---|---|---|
| WO | 2005/014077 | 2/2005 |
| WO | 2005/041810 | 5/2005 |
| WO | 2005/122959 | 12/2005 |
| WO | 2006/028925 | 3/2006 |
| WO | 2006/074476 | 7/2006 |
| WO | 2006/127127 | 11/2006 |

OTHER PUBLICATIONS

U.S. Appl. No. 09/663,111, filed Sep. 15, 2000; Inventor: Davidson et al.

U.S. Appl. No. 09/614,472, filed Jul. 11, 2000; Inventor: Davidson et al.

U.S. Appl. No. 09/325,996, filed Jun. 4, 1999; Inventor: Vardi et al.

Chevalier, M.D., Bernard, "Placement of Coronary Stent in Bifurcation Lesions by the "Culotte" Technique," The American Journal of Cardiology, vol. 82, pp. 943-949 (Oct. 15, 1998).

Nakamura M.D., Shigeru, "Techniques for Palmaz-Schatz Stent Deployment in Lesions with a Large Side Branch," Catheterization and Cardiovascular Diagnosis, vol. 34, pp. 353-361 (1995).

Caputo, Ronald P., "Stent Jail: A Minimum-Security Prison," The American Journal of Cardiology, vol. 77, pp. 1226-1230 (Jun. 1, 1996).

Colombo, M.D., Antonio, ""Kissing" Stent for Bifurcational Coronary Lesions," Catheterization and Cardiovascular Diagnosis, vol. 30, pp. 327-330 (Dec. 1993).

Carrie, M.D., Didier, ""T"-Shaped Stent Placement: A Technique for the Treatment of Dissected Bifurcation Lesions," Catheterization and Cardiovascular Diagnosis, vol. 37 pp. 311-313 (Mar. 1996).

Katoh, M.D., Osamu, "New Double Wire Technique to Stent Ostial Lesions," Catheterization and Cardiovascular Diagnosis, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," American Heart Journal, vol. 127:6, pp. 1600-1607 (Jun. 1994).

Yamashita, M.D., PhD., Takehiro, "Bifurcation Lesions: Two Stents Versus One Stent—Immediate and Follow-up Results," Journal of the American College of Cardiology, vol. 35:5, pp. 1145-1151 (Apr. 2000)

Satler, M.D., Lowell F., "Bifurcation Disease: To Treat or Not to Treat," Catheterization and Cardiovascular Interventions, vol. 50, pp. 411-412 (2000).

* cited by examiner

BIFURCATED STENT WITH ENTIRE CIRCUMFERENTIAL PETAL

CROSS-REFERENCE TO RELATED APPLICATIONS

This application claims the benefit of and priority to U.S. Provisional Application No. 60/850,458, filed Oct. 10, 2006, the entire disclosure of which is hereby incorporated herein by reference in its entirety.

STATEMENT REGARDING FEDERALLY SPONSORED RESEARCH

Not Applicable

FIELD OF THE INVENTION

In some embodiments this invention relates to implantable medical devices, their manufacture, and methods of use. Some embodiments of the invention are directed more specifically to stents and stent designs suitable for use at a vessel bifurcation.

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents and similar devices such as stent, stent-grafts, expandable frameworks, and similar implantable medical devices, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment the invention is directed to a stent having a main body, which has a circumference defining a primary lumen and longitudinal axis extending therethrough. A first region of the main body comprises at least one band disposed circumferentially about the longitudinal axis. A second region of the main body comprises a plurality of interconnected rings concentrically disposed about a side branch opening. An outermost ring extends fully about the circumference of the main body. Each of the rings consist of two longitudinally oriented elements and two circumferentially extending elements.

In some embodiments adjacent rings are engaged directly to one another.

In some embodiments adjacent rings are connected by connectors.

In at least one embodiment the regions of the main body are connected by connectors.

In at least one embodiment, a stent assembly has a main body defining a primary lumen and having a longitudinal axis extending therethrough. The main body further having a proximal end region and a distal end region and a middle region therebetween. The proximal end region and the distal end region each comprise at least one band disposed circumferentially about the longitudinal axis of the main body. The middle region comprises a plurality of interconnected rings disposed concentrically about a side branch opening. One of the rings extends fully about the circumference of the main body. Each of the rings consist of two longitudinally oriented elements and two circumferentially extending elements. In some embodiments the longitudinal elements of the ring extending fully about the circumference of the stent are engaged to one another.

In at least one embodiment, in the expanded state a portion of at least one of the rings extends at an angle oblique to the longitudinal axis and forms a secondary lumen. The secondary lumen disposed about the side branch axis.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
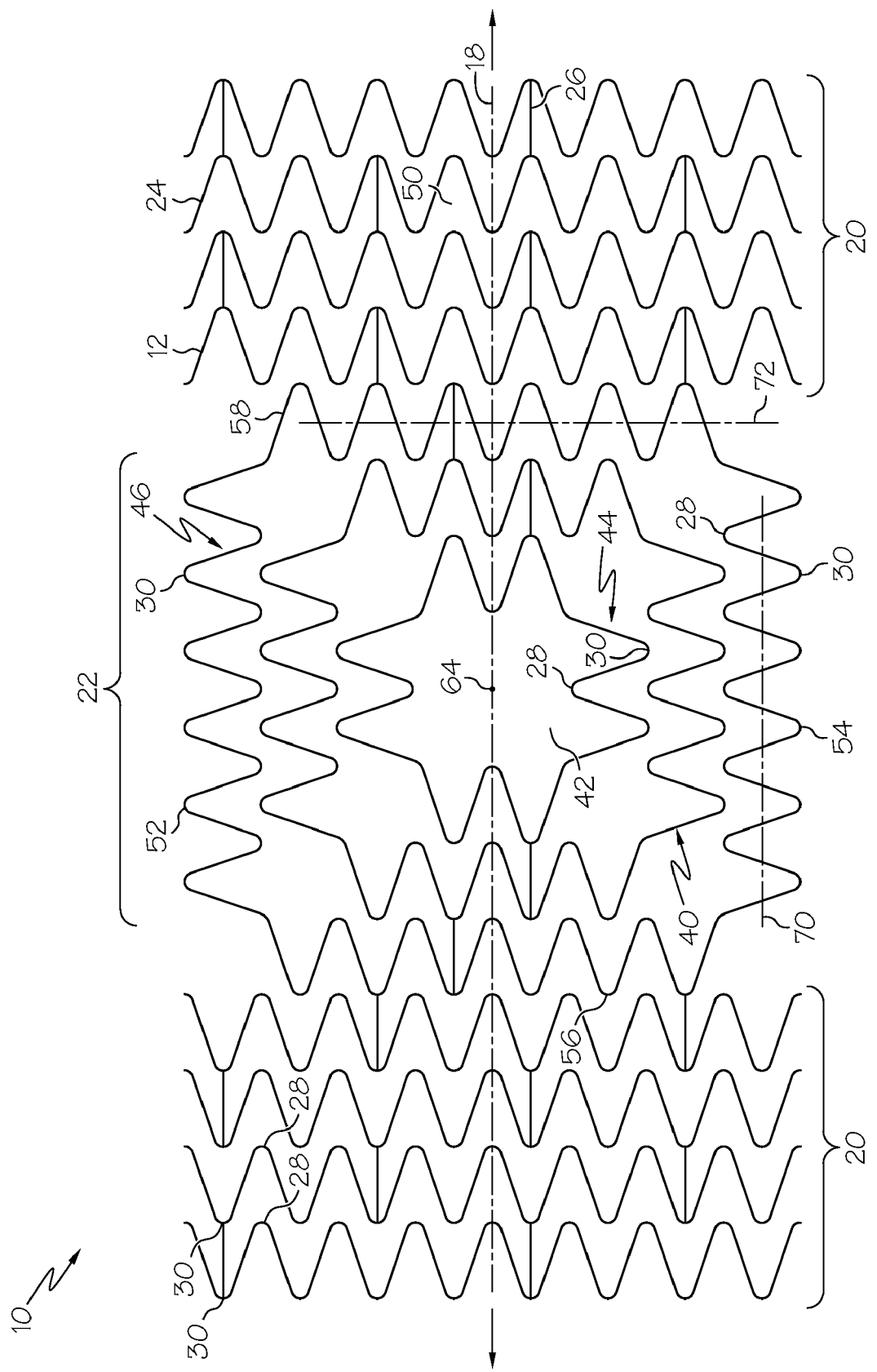
FIG. 1 is a flat view of an embodied bifurcated stent with the smallest concentric ring in the center of the view.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
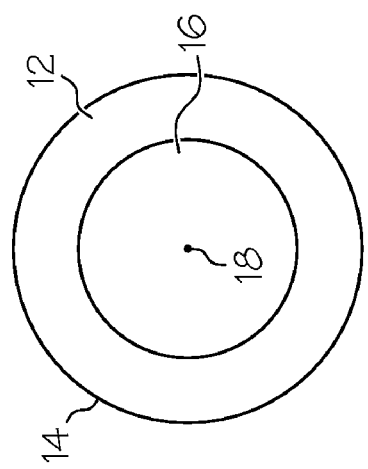
FIG. 2 is a cross-sectional view of the stent of FIG. 1

An embodiment of the invention is shown in FIG. 1, which comprises a flat, top down view of a stent 10, having a main body 12 which defines the stent. The main body 12, such as is shown in FIG. 2 has a circumference 14 and defines a primary lumen 16 therethrough. The main body 12 is disposed about a longitudinal axis 18.

Figure 3:
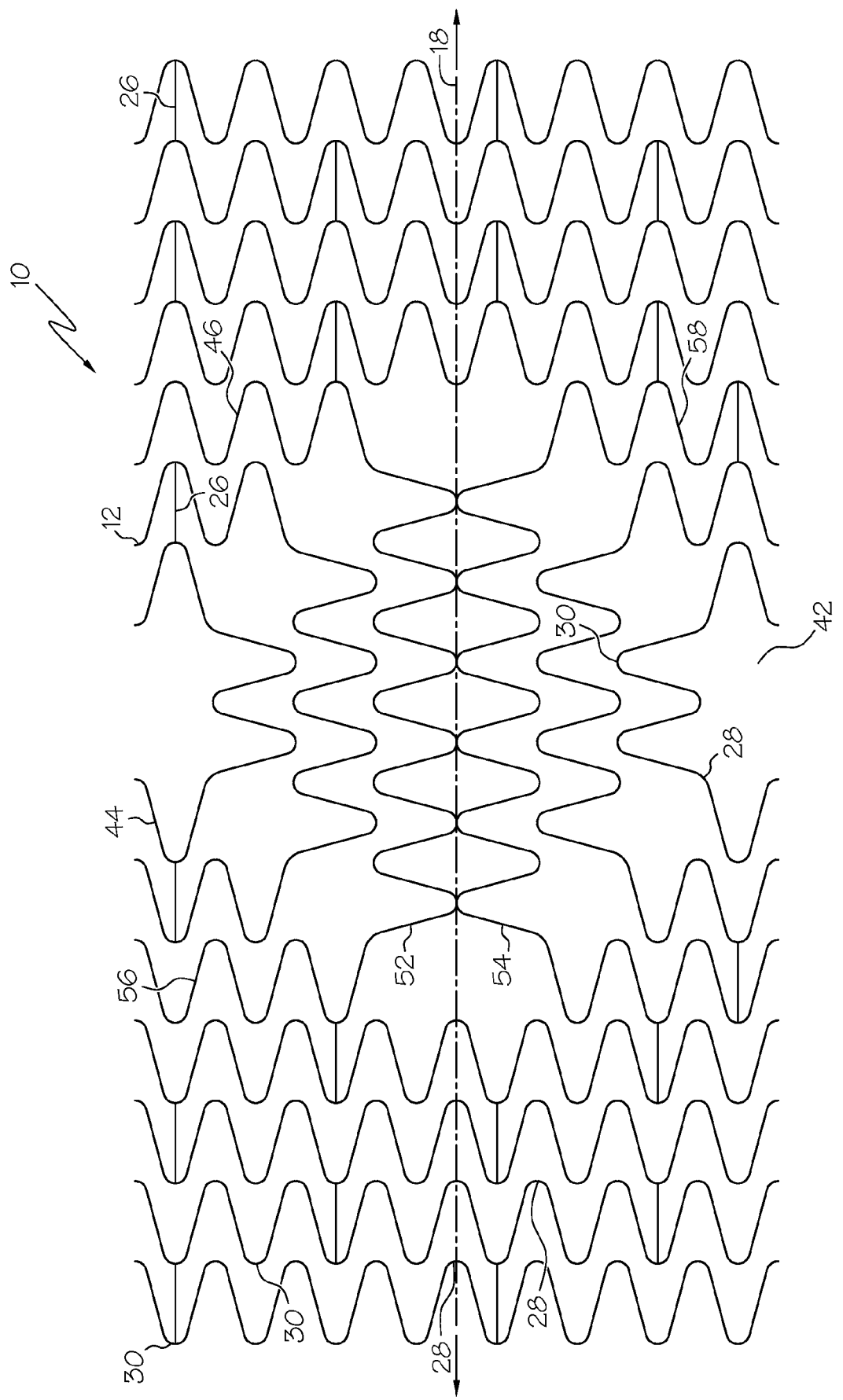
FIG. 3 is a flat view of the stent of FIG. 1 rotated 180 degrees.

The main body, as shown in FIGS. 1 and 3 is provided with a first region 20 and a second region 22.

The first region 20 is comprised of at least one, and in some embodiments several, serpentine bands 24. In the embodiment shown adjacent bands 24 are connected by connectors 26.

The second region 22 of the main body 12 is comprised of rings 40. Rings 40 are concentrically disposed about a side branch opening 42. An innermost ring 44 of the plurality of rings 40 defines the side branch opening 42.

Rings 40 are connected one to the other by connectors 26 in the manner shown. Likewise, an outermost ring 46, of the plurality of rings, is engaged to the bands 24 of the adjacent first region 20 also by connectors 26 in the manner depicted.

In the embodiments shown herein the second or side branch region 22 of the main body 12 is shown positioned substantially between two first regions (proximal and distal) 20. It must be noted however that as dictated by anatomical need and the desires of the practitioner the position of the second region 22 may be anywhere along the length of the stent 10, including but not limited to being positioned at or adjacent to the proximal or distal end of the stent. It should also be understood that, embodiments of the invention include stents having multiple side branch regions.

As is shown in the various embodiments depicted, the adjacent bands 24, rings 40, and connectors 26 define a plurality of stent openings or cells 50. Each cell extends through the main body 12 and is in fluid communication with the primary lumen 16. The side branch opening 42 has an area different than the cells 50. In at least one embodiment the side branch opening 42 has an area greater than any other cell 50. In at least one embodiment the side branch opening 42 has a unique shape, different than any other cell.

Figure 4:
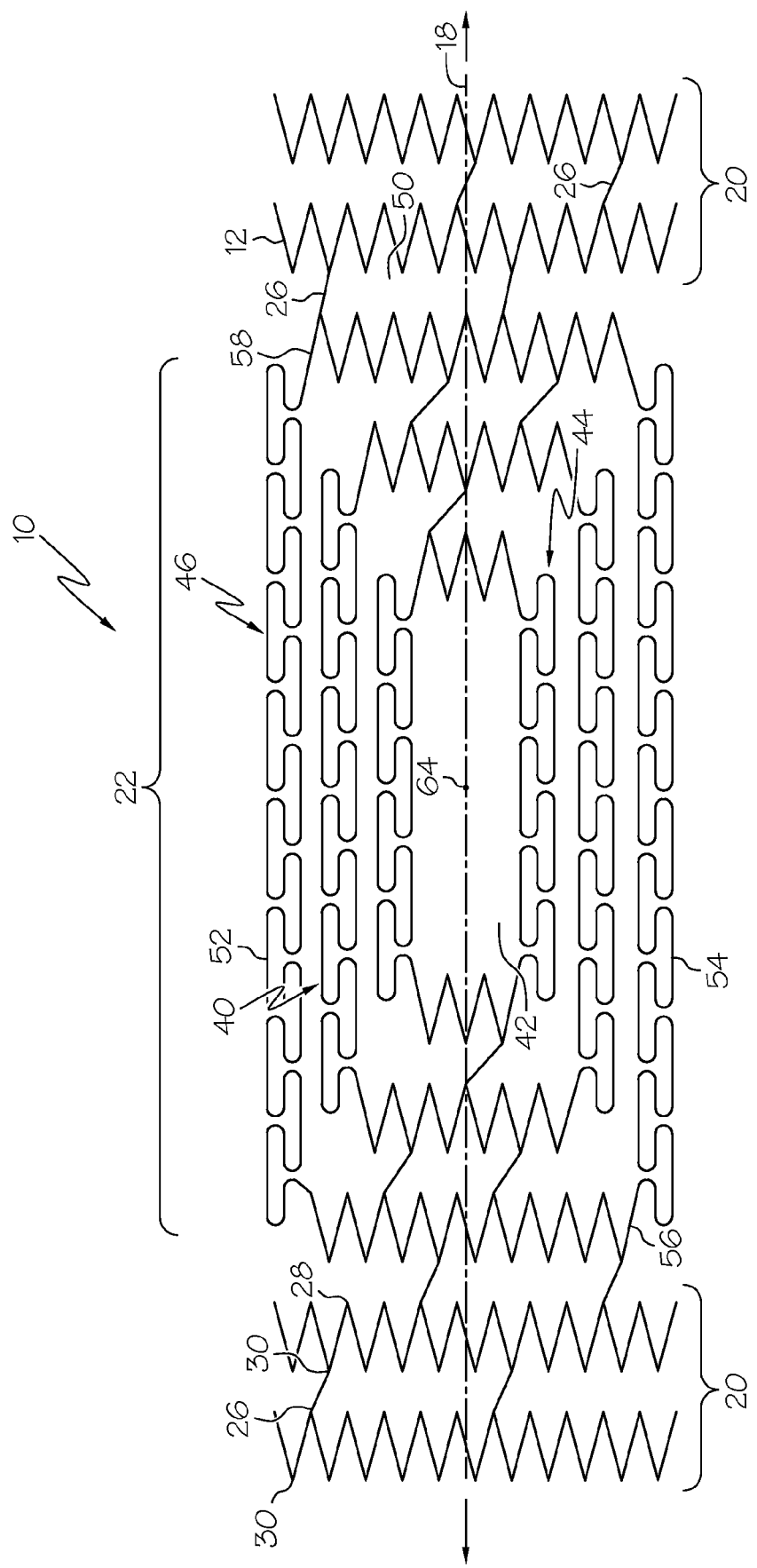
FIG. 4 is a flat view of an embodied bifurcated stent.

Each ring 40, such as are shown in FIGS. 1, 3 and 4, consists of only four elements: first and second longitudinally oriented elements 52 and 54, and first and second circumferential oriented elements 56 and 58. An outermost ring 46 extends completely about the circumference 14 of the main body 12, such as in the manner shown in FIGS. 1 and 4. In at least the embodiment depicted in FIGS. 1 and 3, the longitudinal elements 52 and 54 of the outermost ring 46 are engaged directly one to the other.

In some embodiments of the invention the stent 10 along its entire length has a substantially cylindrical shape in both the unexpanded and expanded states.

Figure 5:
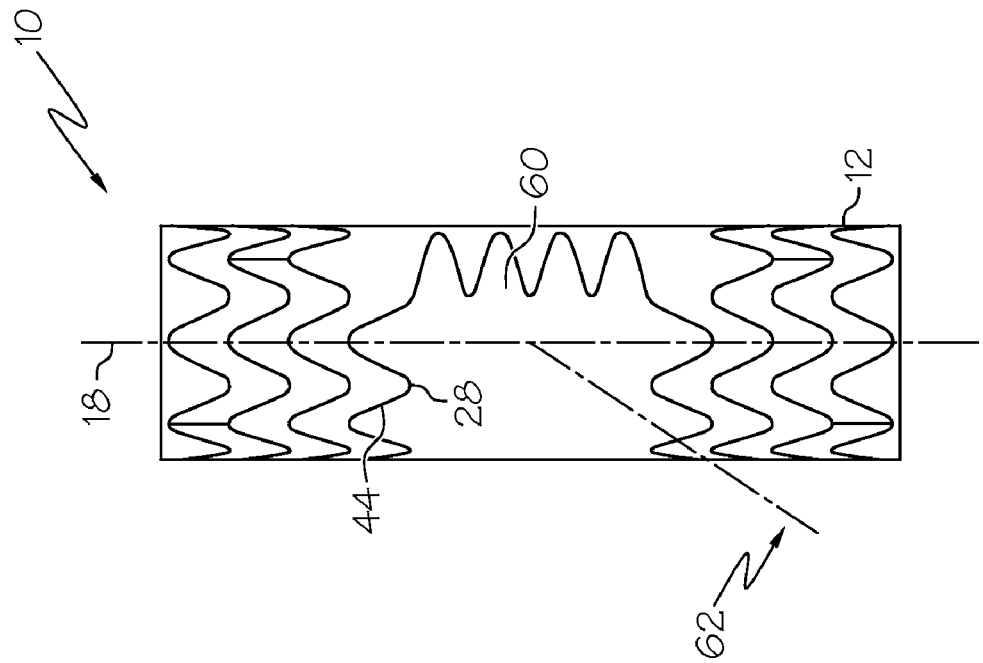
FIG. 5 is a perspective view of an embodied bifurcated stent in the expanded state.

In at least one embodiment however, in the expanded state at least a portion of the second region 22 extends outwardly from the main body 12 at an angle oblique to the longitudinal axis 18 in the manner depicted in FIG. 5.

Rings 40 as depicted in FIG. 1 have a plurality of peaks 28 and valleys 30, wherein peaks 28 are closer in proximity to the center 64 of the side branch opening 42 in the unexpanded state. When fully expanded, in some embodiments the innermost ring 44, or at least one or more peaks 28 of the innermost ring 44, extend outward from the circumferential plane of the main body 12 to form a side branch lumen 60 having a side branch axis 62 extending therethrough. Side branch axis 62 is oblique relative to the longitudinal axis 18.

In at least one embodiment, the flexible nature of the rings 40 allows additional rings, up to and including the outermost ring 46, or portions thereof, to expand outward from the main body 12 to form the side branch lumen 60. Thus, in some embodiments, any or all of the entire side branch region 22 defines a side branch lumen 60 in the expanded state.

In some embodiments, each longitudinally oriented element 52, 54 comprises a repeating waveform defining a straight axis 70 oriented parallel to said longitudinal axis 18. In some embodiments, a longitudinally oriented element 52, 54 comprises alternating peaks 28 and valleys 30. In some embodiments, the peaks 28 of a longitudinally oriented element 52, 54 are aligned with one another in a direction parallel to said longitudinal axis 18, and the valleys 30 of the longitudinally oriented element 52, 54 are aligned with one another in a direction parallel to said longitudinal axis 18. In some embodiments, valleys 30 of one longitudinal element 52 of the outermost ring 46 are directly attached to valleys 30 of the other longitudinal element 54 of the outermost ring 46.

In some embodiments, each circumferentially extending element 56, 58 comprises a repeating waveform defining a straight axis 72 oriented in a stent circumferential direction. In some embodiments, a circumferentially extending element 56, 58 comprises alternating peaks 28 and valleys 30. In some embodiments, the peaks 28 of a circumferentially extending element 56, 58 are aligned with one another in a stent circumferential direction, and the valleys 30 of the circumferentially extending element 56, 58 are aligned with one another in a stent circumferential direction.

The present invention is not limited merely to those embodiments depicted in the enclosed figures. Rather, it should be understood that features of the stent 10 are in some embodiments variable from those depicted in the included figures. For example, in the embodiment shown in FIGS. 1 and 3 bands 24 and rings 40 are shown as having a regular and repeating pattern of interconnected peaks 28 and valleys 30, turns etc. It is noted however that the size, shape, symmetry (or lack thereof), pattern, configuration, etc. of the bands or rings may be varied. Similarly, connectors 26 may be provided with shapes and orientations other than being elongate and substantially parallel to the longitudinal axis 18 as shown.

In the embodiment shown in FIG. 1, each peak 28 of a given band 24 is in circumferential alignment with the longitudinally adjacent peak 28 of a longitudinally adjacent band. In some embodiments however, peaks 28 of adjacent bands are circumferentially offset from one another. In the embodiment depicted in FIG. 4 however, each peak 28 of a given band 24 is circumferentially offset with the peaks of the band longitudinally adjacent thereto.

In the embodiment shown in FIG. 1, between each band 24 extends at least two elongate connectors 26, which engage adjacent bands in a valley 30 to valley 30 configuration, and which are substantially parallel to the longitudinal axis 18. In the embodiment depicted in FIG. 4 however, the connectors 26 engage adjacent bands in a peak 28 to valley 30 configuration, wherein each connector 26 is angled or offset from the longitudinal axis 18.

In some embodiments, adjacent bands 24 are connected directly one to the other without the use of connectors.

In some embodiments, any number of connectors 26 are present between bands 24. In some embodiments the connectors 26 extend peak to valley, peak to peak, etc. In some embodiments one or more connectors 26 include one or more elongate portions, one or more curved portions, one or more angled portions, etc. In some embodiments, one or more connectors 26 or at least a portion thereof is angled relative to the longitudinal axis 18.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Some other examples of therapeutic agents include everolimus and sirolimus, their analogs and conjugates. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof Where the therapeutic agent includes a polymer agent, the polymer agent may be a polystyrene-polyisobutylene-polystyrene tri-block copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below. This completes the description of the invention. Those skilled in the art may recognize other equivalents to the specific embodiment described herein which equivalents are intended to be encompassed by the claims attached hereto.

The invention claimed is:

1. A stent comprising:
  a main body having a circumference defining a primary lumen and having a longitudinal axis extending therethrough, the main body having a first region and a second region, the first region comprising at least one band disposed circumferentially about the longitudinal axis of the main body,
  the second region comprising a plurality of interconnected rings concentrically disposed about a side branch opening, the side branch opening being in fluid communication with the primary lumen, an outermost ring occupying a full circumference of the main body, each of the interconnected rings consisting of two longitudinally oriented elements and two circumferentially extending elements, wherein each longitudinally oriented element comprises a repeating waveform defining a straight axis oriented parallel to said longitudinal axis.

2. The stent of claim 1 further comprising a third region, the third region comprising at least one band disposed circumferentially about the longitudinal axis of the main body, the second region positioned between the first region and the third region.

3. The stent of claim 1 wherein adjacent bands and adjacent rings define a plurality of openings, the side branch opening having an area different than any of the plurality of openings.

4. The stent of claim 3 wherein the stent has an unexpanded state and an expanded state, wherein in both the unexpanded state and the expanded state the main body defines a substantially cylindrical shape.

5. The stent of claim 3 wherein the stent has an unexpanded state and an expanded state, in the unexpanded state the main body having a substantially cylindrical shape, in the expanded state at least a portion of the second region extending at an angle oblique to the longitudinal axis.

6. The stent of claim 5 wherein the at least a portion of the second region comprises an inner most ring, the inner most ring defining the side branch opening, in the expanded state at least a portion of the inner most ring defining a side branch lumen having a side branch axis extending therethrough, the side branch axis extending at the angle oblique to the longitudinal axis.

7. The stent of claim 6 wherein in the unexpanded state the side branch opening defines a center, and each element of the inner most ring comprises a serpentine shape having a plurality of interconnected peaks and valleys, wherein each peak is closer in proximity to the center than each valley.

8. The stent of claim 1 wherein the first region and the second region are connected by at least one connector.

9. The stent of claim 1 wherein adjacent rings are connected by at least one connector.

10. The stent of claim 1 wherein the longitudinal elements of the outermost ring are directly engaged one to the other.

11. The stent of claim 10 wherein the longitudinal elements of the outer most ring comprise a first longitudinal element and a second longitudinal element, each longitudinal element comprising a serpentine shape having a plurality of interconnected peaks and valleys,
at least one valley of the first longitudinal element being longitudinally aligned with at least one valley of the second longitudinal element,
wherein the at least one valley of the first longitudinal element and the at least one valley of the second longitudinal element are directly engaged one to the other.

12. The stent of claim 11 wherein each valley of the first longitudinal element is engaged to a longitudinally aligned valley of the second longitudinal element.

13. The stent of claim 1 wherein at least a portion of the main body is self expandable.

14. The stent of claim 1 wherein at least a portion of the main body is balloon expandable.

15. The stent of claim 1 wherein at least a portion of the main body further comprises a therapeutic agent.

16. The stent of claim 1 wherein at least a portion of the main body is radiopaque.

17. The stent of claim 1, wherein each circumferentially extending element comprises a repeating waveform defining an axis oriented in a stent circumferential direction.

18. The stent of claim 17 wherein each circumferentially extending element comprises alternating peaks and valleys, each peak of a respective circumferentially extending element aligned on a common circumference of the main body.

19. The stent of claim 18 wherein each valley of a respective circumferentially extending element is aligned on a common circumference of the main body.

20. The stent of claim 1, wherein each longitudinally oriented element comprises alternating peaks and valleys, said peaks aligned in a direction parallel to said longitudinal axis.

21. A stent assembly comprises:
a main body defining a primary lumen and having a longitudinal axis extending therethrough, the main body having a proximal end region, a distal end region and a middle region therebetween,
the proximal end region and the distal end region each comprise at least one band disposed circumferentially about the longitudinal axis of the main body,
the middle region comprises a plurality of interconnected rings disposed concentrically about a side branch opening in fluid communication with the primary lumen, one of the rings occupying a full circumference of the main body, wherein each of the interconnected rings consist of two longitudinally oriented elements and two circumferentially extending elements.

22. The stent of claim 21 wherein the longitudinal elements of the ring that occupies a full circumference of the stent are directly engaged to one another.

23. A stent comprising:
an expandable framework having primary lumen therethrough, the expandable framework defining a longitudinal axis, the expandable framework having a proximal end region, a distal end region and a middle region therebetween,
the proximal end region and the distal end region each comprising at least one band coaxial with said longitudinal axis,
the middle region comprising a first side branch ring and a second side branch ring, the first side branch ring defining a side branch opening in fluid communication with the primary lumen, the second side branch ring extending concentrically around the first side branch ring, each of said side branch rings consisting of two longitudinally oriented elements and two circumferentially extending elements, each circumferentially extending element comprising a repeating waveform defining an axis oriented in a stent circumferential direction, each longitudinally oriented element comprising a repeating waveform defining a straight axis oriented parallel to said longitudinal axis;
wherein the second side branch ring occupies a full circumference of the expandable framework.

* * * * *